(12) United States Patent
Chen et al.

(10) Patent No.: US 11,666,908 B2
(45) Date of Patent: Jun. 6, 2023

(54) MICROFLUIDIC PACKAGE

(71) Applicant: HEWLETT-PACKARD DEVELOPMENT COMPANY, L.P., Spring, TX (US)

(72) Inventors: Chien-Hua Chen, Corvallis, OR (US); Michael W. Cumbie, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 43 days.

(21) Appl. No.: 16/608,408

(22) PCT Filed: Sep. 14, 2017

(86) PCT No.: PCT/US2017/051467
§ 371 (c)(1),
(2) Date: Oct. 25, 2019

(87) PCT Pub. No.: WO2019/055007
PCT Pub. Date: Mar. 21, 2019

(65) Prior Publication Data
US 2020/0197935 A1    Jun. 25, 2020

(51) Int. Cl.
*B01L 3/00* (2006.01)
*B29C 70/68* (2006.01)
*B29K 63/00* (2006.01)
*B29L 31/00* (2006.01)

(52) U.S. Cl.
CPC ... *B01L 3/502715* (2013.01); *B01L 3/502707* (2013.01); *B29C 70/68* (2013.01); *B01L 2200/12* (2013.01); *B01L 2300/06* (2013.01); *B01L 2300/0627* (2013.01); *B01L 2300/0816* (2013.01); *B29K 2063/00* (2013.01); *B29L 2031/752* (2013.01)

(58) Field of Classification Search
CPC ............ B01L 3/5027; B01L 3/502715; B01L 2300/06; B01L 2300/0627
See application file for complete search history.

(56) References Cited

U.S. PATENT DOCUMENTS

| | | | |
|---|---|---|---|
| 7,419,639 B2 | 9/2008 | Osterfeld et al. | |
| 7,563,614 B2 * | 7/2009 | Orwar | B82Y 20/00 422/417 |
| 8,007,078 B2 | 8/2011 | Haluzak et al. | |
| 9,128,028 B2 | 9/2015 | McBrady et al. | |
| 2002/0041827 A1 * | 4/2002 | Yager | G01N 30/0005 422/400 |

(Continued)

FOREIGN PATENT DOCUMENTS

| | | |
|---|---|---|
| EP | 2062644 A1 | 5/2009 |
| WO | WO-2014178726 A1 | 11/2014 |

OTHER PUBLICATIONS

Grist, S. M. et al., Optical Oxygen Sensors for Applications in Microfluidic Cell Culture. ISSN 1424-8220; Oct. 15, 2010, <www.mdpi.com/1424-8220/10/10/9286/pdf>.

*Primary Examiner* — Brian J. Sines
(74) *Attorney, Agent, or Firm* — Foley & Lardner LLP (57) ABSTRACT

A microfluidic package may include a fluid passage, a substrate having a substrate surface adjacent an interior of the fluid passage and components inset in the substrate, the components having component surfaces adjacent the fluid passage and substantially flush with the substrate surface.

20 Claims, 4 Drawing Sheets

(56) References Cited

U.S. PATENT DOCUMENTS

| | | |
|---|---|---|
| 2005/0241959 A1 | 11/2005 | Ward et al. |
| 2008/0199362 A1 | 8/2008 | Chong et al. |
| 2009/0169427 A1* | 7/2009 | Supriya .................. B05D 5/00 |
| | | 422/68.1 |
| 2010/0297780 A1 | 11/2010 | De Theije et al. |
| 2016/0220993 A1 | 8/2016 | Koltermann |
| 2019/0070606 A1* | 3/2019 | Li .................... B01L 3/502715 |
| 2019/0119104 A1* | 4/2019 | Chen .................. G01P 15/0802 |

* cited by examiner

MICROFLUIDIC PACKAGE

BACKGROUND

Many applications involve the testing or alteration of a fluid. With such applications, the fluid is often directed to multiple components that sense or alter the fluid. Microfluidic passages may be used to transmit small volumes of fluid between the multiple components.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Microfluidic devices involve relatively small volumes of a fluid or involve microfluidic passages. Components along such small microfluidic passages often interfere with the smooth flow of fluid across or to different components of the microfluidic devices. The components along the microfluidic passages may form dead spaces that create areas of fluid stagnation in the microfluidic passage. The size of the components may further demand larger microfluidic passages which may increase the size and fluid volume demands of the microfluidic device.

Disclosed herein are example microfluidic packages and methods that embed components, such as microfluidic dies, in a substrate along a microfluidic passage, wherein the components are substantially flush with a surface of the substrate along the microfluidic passage. As a result, the microfluidic packages and methods may provide smoother fluid flow, may facilitate more compact microfluidic packages and may allow use of the microfluidic package with smaller volumes of the fluid being tested or altered.

For purposes of this disclosure, the term "substantially flush" with respect to two surfaces means that the two surfaces are within 10 μm of one another. The term "flush" with respect to two surfaces means that the two surfaces are coplanar. Throughout the disclosure, passage or channels may be referred to as "microfluidic". As used herein a microfluidic channel or passage may correspond to a channel or passage of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.). Such microfluidic channels or passages may be formed by performing etching, microfabrication (e.g., photolithography), micromachining processes, or any combination thereof in a substrate of the fluidic die. Some example substrates may include silicon based substrates, glass based substrates, gallium arsenide based substrates, and/or other such suitable types of substrates for microfabricated devices and structures. Accordingly, microfluidic channels, passages, chambers, orifices, and/or other such features may be defined by surfaces fabricated in the substrate of a fluidic die.

Disclosed is an example microfluidic package that comprises a fluid passage, a substrate having a substrate surface adjacent an interior of the fluid passage and components inset in the substrate. The components comprise component surfaces adjacent the fluid passage that are substantially flush with the substrate surface.

Disclosed is an example method for forming a microfluidic package. The method may involve embedding heterogeneous components in a substrate surface of a substrate such that the heterogeneous components have surfaces substantially flush with the substrate surface. The method may further involve forming a fluid passage adjacent the substrate surface with the substrate surface and the heterogeneous components forming an interior surface of the fluid passage.

Disclosed is an example microfluidic package that comprises a fluid passage, a substrate having a substrate surface adjacent an interior of the fluid passage and component dies inset in the substrate. The component dies may have component surfaces that are adjacent the fluid passage and that are substantially flush with the substrate surface.

Figure 1:
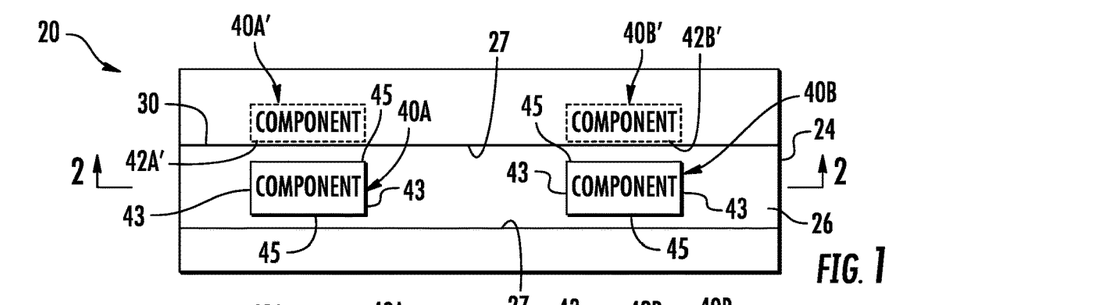
FIG. 1 is a top view schematically illustrating an example microfluidic package.
Figure 2:
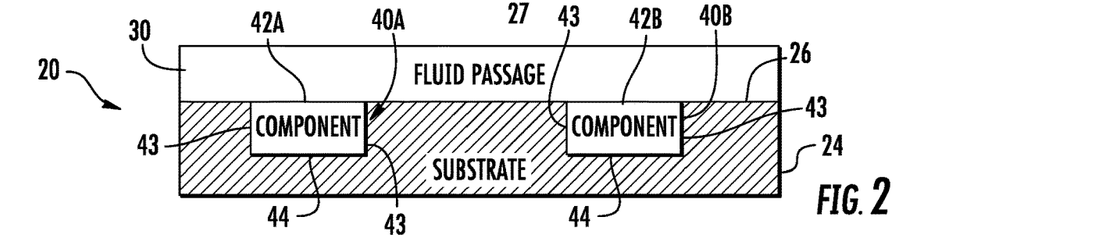
FIG. 2 is a sectional view of the example microfluidic package of FIG. 1 taken along line 2-2.

FIGS. 1 and 2 schematically illustrates portions of an example microfluidic package 20. FIG. 1 is a top view of microfluidic package 20 2 is a sectional view of microfluidic package 20. Microfluidic package 20 may provide smoother fluid flow, may be more compact and may allow use of smaller volumes of the fluid being tested or altered. Microfluidic package 20 comprises substrate 24, fluid passage 30 and components 40A, 40B (collectively referred to as components 40).

Substrate 24 comprises at least one layer of material at least partially defining an interior wall or surface of fluid passage 30. In one implementation, substrate 24 has an exterior surface 26 which forms a floor surface of fluid passage 30. In such an implementation, a separate layer of material formed on top of or adjacent to substrate 24 forms fluid passage 30. It should be appreciated that electrically conductive traces or wiring, although not illustrated, may additionally be formed within or on substrate 24.

In some implementations, substrate 24 may have an exterior surface that forms an interior side wall surface or an exterior surface that forms interior ceiling surface of fluid passage 30. For example, substrate 24 may have a groove therein that forms a fluid passage 30, wherein substrate 24 additionally comprises surfaces 27 that form one or both sidewalls of fluid passage 30. In yet other implementations, substrate 24 may include a through opening or bore such that substrate 24 completely surrounds fluid passage 30, forming the floor, sidewalls and ceiling of fluid passage 30. In one implementation, substrate 24 is formed from a moldable material such as an epoxy mold compound (EMC). In yet other implementations, substrate 24 may be formed from other moldable materials.

In some implementations, substrate 24 may be formed from a non-moldable material, wherein portions of substrate 24 are removed to form at least one cavity that receives components 40. For example, a separate cavity may be formed in substrate 24 for each of the to be received components 40. In such implementations, components 40 are subsequently inserted into the formed cavities.

Fluid passage 30 comprise a microfluidic channel or passage extending across components 40. As discussed above, in one implementation, fluid passage 30 may be formed by a separate layer deposited upon or adjacent to substrate 24. In other implementations, fluid passage 30 may be formed by a groove or channel formed in substrate 24. Microfluidic passage 30 has an interior surface, a first portion of which is defined or bordered by substrate 24 and a second portion of which is defined or bordered by an outer surface of each of components 40. In the example illustrated in which surface 26 of substrate 24 forms a floor of fluid passage 30, the upper surfaces of components 40 form a portion of the floor. As shown by broken lines, in other implementations in which surfaces 27 of substrate 24 forms an interior side of fluid passage 30, components 40 may alternatively or additionally be positioned such that their exterior surfaces form portions of the interior side of fluid passage 30. In some implementations, in which substrate 24 also forms a ceiling of fluid passage 30, components 40 may be positioned are inset within the ceiling so as to form a portion of the ceiling of fluid passage 30. In one implementation, fluid passage 30 comprise a three sided passage. In another implementation, fluid passage 30 is surrounded on all sides.

Components 40 comprise distinct devices that are received or inset into substrate 40 such that components 40 having component surfaces that are adjacent fluid passage 30 and substantially flush with the surface 26 of substrate 24. For purposes of this disclosure, a "component surface" refers to an exterior most surface of a component. In the example illustrated, components 40A and 40B have component surfaces 42A and 42B, respectively, that extend flush with surface 26 of substrate 24 and that form an interior surface of fluid passage 30. The remaining component surfaces 43, 44 and 45 of each of components 40 extend opposite to or face portions of substrate 24. As indicated by broken lines, in other implementations, components 40A' and 40B' may additionally or alternatively positioned in substrate 24 such that surfaces 42' are substantially flush with one of surfaces 27 of substrate 24, facing sideways and forming an interior side surface of fluid passage 30.

Because component surfaces 42A, 42B and/or 42A', 42B' are each substantially flush with surface 26 and/or surface 27, surfaces 42A, 42B and/or 42A', 42B' interfere with the flow of fluid along fluid passage 30 to a lesser extent. At the same time, because the remaining component surfaces of components 40 oppose substrate 24, rather than the flow of fluid along fluid passage 30, the remaining component surfaces 43, 44 and 45 of components 40 do not substantially project into fluid passage 30 and do not interfere with the flow of fluid therethrough. Because the extent to which components 40 project into fluid passage 30 is reduced, the size of fluid passage 30 may be reduced while allowing a sufficient fluid flow, reducing the size of package 20.

In one implementation, components 40 are heterogeneous, not being similar to one another in at least one of size, shape, interior structure or function. In one implementation, components 40 at the same size and shape, perform different functions. In another implementation, components 40 perform the same function, but have different sizes, shapes and/or internal electronics. For example, in one implementation, component 40A may comprise one of a die having an integrated electronic circuit, a glass waveguide, metallic antenna, optical sensor, a chemical sensor, a semiconductor laser or the like while component 40B comprises a different one of a die having an integrated electronic circuit, a glass waveguide, metallic antenna, optical sensor, a chemical sensor, a semiconductor laser or the like.

In one implementation, components 40 may comprise similar or identical electronic dies, dies having electronic circuitry. For example, components 40 may comprise a semiconductor laser, a chemical sensor, an optical sensor or another die having integrated circuitry. In contrast to a device or die completely surrounded and encapsulated within a substrate and merely having an electrode or other touch point extending to a point of exposure with respect to the microfluidic passage, at least one surface of the electronic die of each of components 40, itself, extends adjacent to fluid passage 30 and forms an interior surface of fluid passage 30. Such a location of a die itself may facilitate a more compact microfluidic package and may facilitate enhanced sensing or other performance of one or both of components 40.

Figure 3:
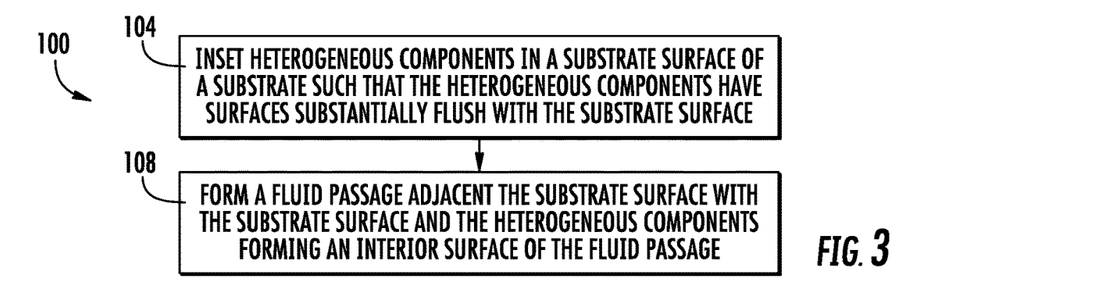
FIG. 3 is a flow diagram of an example method for forming a microfluidic package.

FIG. 3 is a flow diagram of an example method 100 for forming an example microfluidic passage. Method 100 may be used to form a microfluidic package that provides enhanced fluid flow relative to multiple components 40 situated along the fluid passage. Although method 100 is described in the context of being carried out form microfluidic package 20, it should be appreciated that method 100 may likewise be utilized to form any of the microfluidic packages described herein or other similar microfluidic packages.

As indicated by block 104, components, such as components 40, are inset in a substrate surface 26 of a substrate 24 such that the components 40 have surfaces 42 which are substantially flush with the substrate surface 26. In the example illustrated, the components 40 may be heterogeneous. In other implementations, components 40 may be dies having integrated circuitry.

As indicated by block 108, a fluid passage 30 is formed adjacent to the substrate surface 26 with the substrate surface 26 and the components 40 forming an interior surface of the fluid passage 30. In one implementation, the fluid passage 30 may be formed by forming a separate layer or multiple layers adjacent to or on top of substrate 24. In yet another implementation, a groove or passage may be formed in substrate 24, wherein substrate 24 forms sidewalls of the fluid passage in addition to a floor or ceiling of the fluid passage 30.

Figure 4:
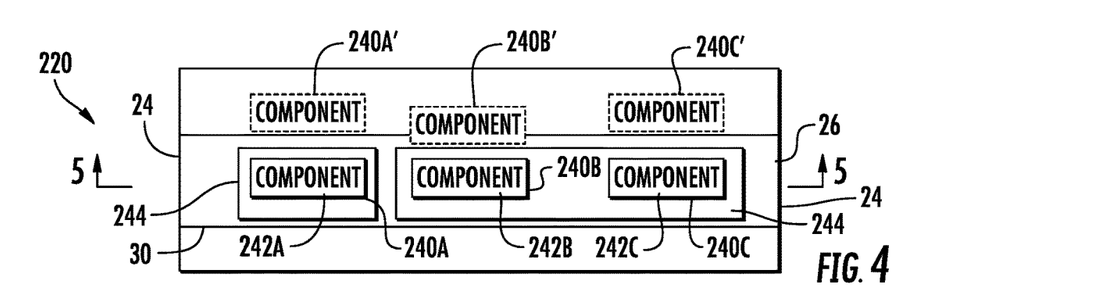
FIG. 4 is a top view schematically illustrating an example microfluidic package.
Figure 5:
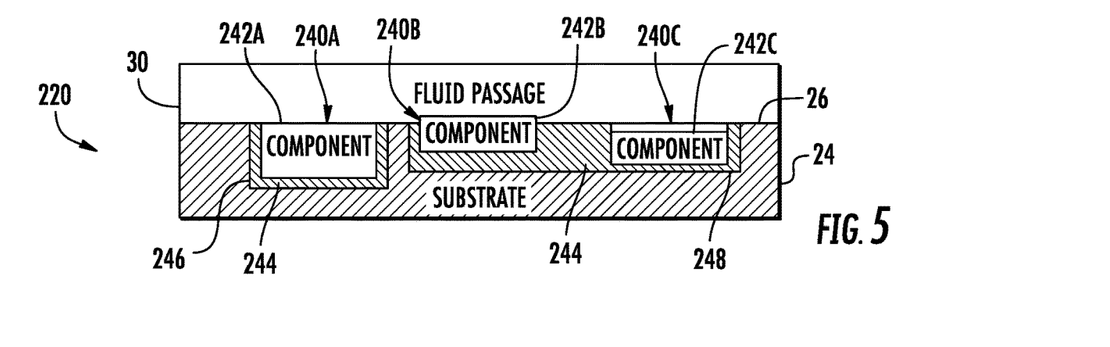
FIG. 5 is a sectional view of the example microfluidic package of FIG. 4 taken along line 5-5.

FIGS. 4 and 5 schematically illustrate portions of another example microfluidic package 220. FIGS. 4 and 5 illustrate various examples of insetting components 40 with respect to a surface, such as surface 26, of substrate 24. Microfluidic package 220 is similar to microfluidic package 20 except that microfluidic package 220 comprises components 240A, 240B and 240C (collectively referred to as components 240)

which are inset with respect to substrate 24 in various example fashions. Those remaining structures of microfluidic package 220 which correspond to structures of microfluidic package 20 are numbered similarly.

Components 240 are heterogeneous, not being similar to one another in at least one of size, shape, interior structure or function. For example, in one implementation, components 240 may each comprise a different one of: (a) a die having an integrated electronic circuit, (b) a glass waveguide, (c) a metallic antenna, (d) and optical sensor, (e) a chemical sensor or (f) a semiconductor laser. In one implementation, each of components 240 comprises a die having an integrated circuit formed therein.

As further shown by FIG. 5, components 240 are differently inset and substantially flush with respect to surface 26. Component 240A has a component surface 242A that is flush, level or coplanar with surface 26. Component 240B has a component surface 242B that slightly projects or protrudes above surface 26, but less than 10 μm and, in one implementation, less than 2 μm above surface 26. Component 240C as a component surface 242C that is slightly recessed below the surface 26, but less than 10 μm and, in one implementation, less than 2 micrometers below surface 26. As shown by broken lines, in implementations where substrate 24 forms an interior side wall of fluid passage 30, components 240A', 240B' and 240C' may additionally or alternatively be inset within substrate 24 so as to form interior sides or a ceiling of fluid passage 30.

In the example illustrated, each of components 240 are surrounded or encapsulated on multiple sides, but for surfaces 242, by a filler material 244. In the example illustrated, package 220 comprises cavities 246, 248 extending into substrate 24. Cavity 246 is sized larger than the component 240A while cavity 248 is sized larger than components 240B and 240C. In one implementation, cavities 246, 248 are molded into substrate 24. In another implementation, cavities 246, 248 are formed in substrate 24 by material removal techniques that remove material from substrate 24. Cavity 246 receives component 240A while cavity 248 receives both of components 240B and 240C.

Filler material 244 comprise a soft, compliant, deformable or moldable material, such as epoxy mold compound, that may be cured, solidified or hardened following receipt of components 240 by cavities 246, 248. Filler material 244 fills cavities 246 and 248 between components 240 and substrate 24. At the same time, filler material 244 maintains exposure of surfaces 242 of components 240 with respect to the interior of fluid passage 30. The filler material 244 may assist in retaining the component 240 within the larger cavity. The filler material 244 further provides a smooth level surface along the interior fluid passage 30 to further facilitate smooth fluid flow within fluid passage 30.

Figure 6:
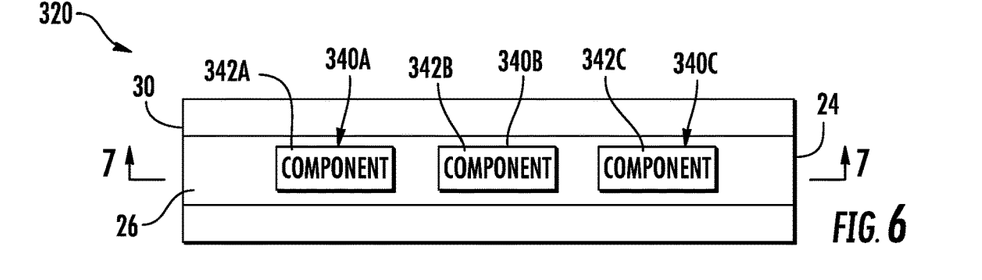
FIG. 6 is a top view schematically illustrating an example microfluidic package.
Figure 7:
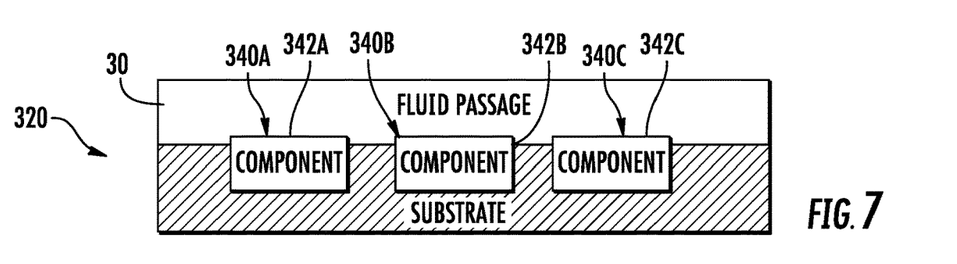
FIG. 7 is a sectional view of the example microfluidic package of FIG. 6 taken along line 7-7.

FIGS. 6 and 7 schematically illustrate portions of another example microfluidic package 320. FIG. 6 is a top view of package 320 while FIG. 7 is a sectional view of package 320. Package 320 is similar to package 20 except that component surfaces 342A, 342B and 342C (collectively referred to as surfaces 342) of each of the components 340A, 340C and 340D (collectively referred to as components 340), respectively, are not flush, but merely substantially flush with surface 26 of substrate 24. Surfaces 342 are further coplanar with one another. The exposed component surfaces 342 extend in a single plane parallel to the plane containing surface 26. Because component surfaces 342 are coplanar, components 342 facilitate smoother fluid flow through and along fluid passage 30.

In one implementation, components 340 are heterogeneous, not being similar to one another in at least one of size, shape, interior structure or function. For example, in one implementation, components 240 may each comprise a different one of: (a) a die having an integrated electronic circuit, (b) a glass waveguide, (c) a metallic antenna, (d) and optical sensor, (e) a chemical sensor or (f) a semiconductor laser. In another implementation, each of components 340 comprises a die having an integrated circuit formed therein, wherein components 340 may or may not be heterogeneous.

Figure 8:
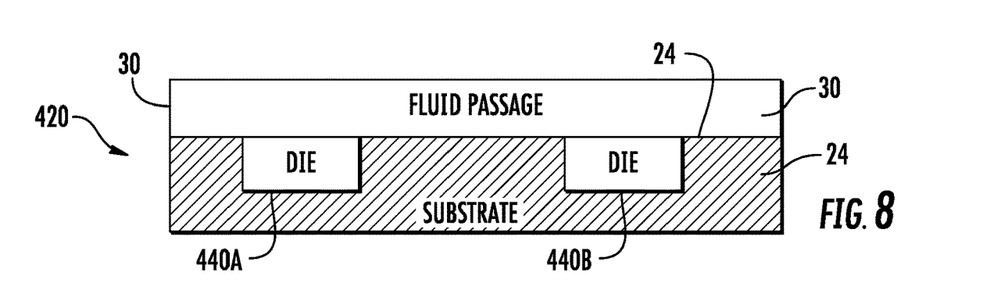
FIG. 8 is a sectional view of an example microfluidic package.

FIG. 8 is a sectional view schematically illustrating portions of another example microfluidic package 420. FIG. 1 also depicts a top view of microfluidic package 320. Microfluidic package 420 is similar to microfluidic package 20 described above except package 420 is explicitly illustrated as comprising similar dies 440A and 440B (collectively referred to as dies 440) in place of components 40A and 40B. As with components 40, dies 440 are substantially flush with surface 26 of substrate 24 along and adjacent to fluid passage 30. In the example illustrated, dies 440 are flush with surface 26 and are coplanar with one another. In one implementation, dies 440 comprise sensing dies. Because dies 440 are exposed directly to the interior of fluid passage 30, dies 440 may better carryout sensing functions with respect to the fluid flowing through fluid passage 30.

Figure 9:
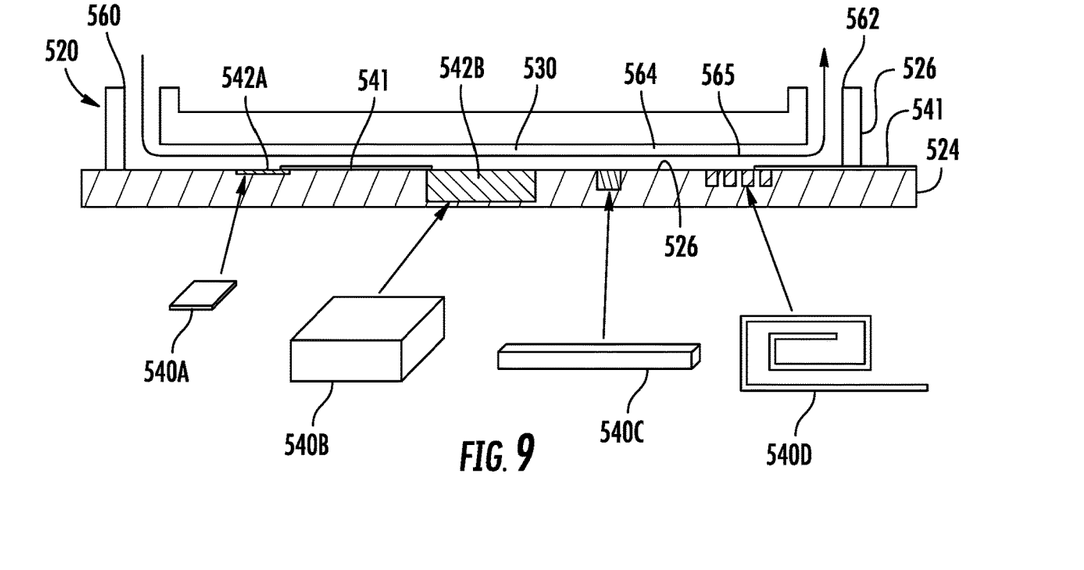
FIG. 9 is a sectional view of an example microfluidic package, with components additionally illustrated in detail separate from the sectional view.

FIG. 9 is a sectional view illustrating portions of another example microfluidic package 520. Microfluidic package 520 comprises substrate 524, fluid passage layer 526 forming fluid passage 530, package components 540A, 540B, 540C and 540D (collectively referred to as components 540) and electrical connections 541. Components 540 are further illustrated as being exploded out from the sectional view.

Substrate 524 is similar to substrate 24 described above. Substrate 524 forms a base or foundation of one or more layers of material in which components 540 are inset. In the example illustrated, each of components 540 are embedded into substrate 524. In the example illustrated, substrate 524 comprises a layer of a molded material, such as a layer of solidified or cured epoxy mold compound which encapsulates or is over molded about the bottom and sides of each of components 540.

Fluid passage layer 526 comprises at least one layer of material formed adjacent to substrate 524. Fluid passage layer 526 forms fluid passage 530. As shown by FIG. 9, fluid passage 530 has an inlet 560, an outlet 562 and a main passage portion 564 that extends over and across each of components 540. In the example illustrated, fluid flows through fluid passage 530 in the direction indicated by arrow 565.

Components 540 comprise components that are inset and substrate 524 adjacent to fluid passage 530 such that exterior surfaces of components 540 extend adjacent to, directly in contact with, the interior of fluid passage 530. In the example illustrated, components 540A, 540B, 540C and 540D have component surfaces 542A, 542B, 542C, 542D (collectively referred to as component surfaces 542), respectively, facing and extending adjacent to the fluid passage 530. Each of component surfaces 542 is flush with surface 526 of substrate 524. Each of component surfaces 542 are coplanar with one another and coplanar with surface 526. In other implementations, surfaces 542 may not be coplanar with one another and may not flush with surface 526. For example, in some implementations, surfaces 542 may slightly project above or be slightly recessed below surface 526, was still being substantially flush with surface 526.

In the example illustrated, component 540A comprises a thin die having integrated circuit. In one implementation, component 540A has a thickness of less than or equal to 100 µm and nominally 50 µm. Component 540B comprises a relatively thick die having integrated circuit. In one implementation component 540B has a thickness greater than 100 µm and, in one implementation, greater than 500 µm. In the example illustrated, component 540B comprise a die having a thickness of greater than 700 µm.

In the example illustrated, component 540C comprises a waveguide, a mass of material that conveys electromagnetic waves. In one implementation, component 540C comprise a tube or bar of a glass material or other optically transmissive material. In the example illustrated, component 540C has a thickness of at least 200 µm and nominally 500 µm.

In the example illustrated, component 540D comprises an antenna for the receipt or transmission of signals. In one implementation, component 540D comprises an antenna formed from a metal, such as copper. Component 540D may have a thickness of at least 100 µm and, in one implementation, greater than 200 µm.

As shown by FIG. 9, the thickness of substrate 524 accommodates the varying thicknesses of the various components 540. In one implementation, component 540 are embedded in the material forming substrate 524. As will be described hereafter, in one implementation, components 540 are molded into substrate 524 or substrate 524 is over molded about components 540. In other implementations, components 540 may be inset in substrate 524 in other manners, such as described above with respect to microfluidic package 220.

Electrical connections 541 electrically connect some of components 540 to one another or to external electronics. In the example illustrated, electrical connections 541 electrically connect components 540A and 540B to one another. Electrical connections 541 further connect component 540C to external componentry or electronics. In one implementation, electrical connections 541 comprise wires or traces formed of electrically conductive material that extend along or are inset with respect to surface 526 of substrate 524. In other implementations, electrical connections 541 may comprise electrically conductive traces formed on a bottom side of substrate 541 and connected to particular components 540 through vias in substrate 524. In yet other implementations, electrical connections 541 may comprise electrically conductive traces or wires formed within the material or layer forming substrate 524. In some implementations, electrical connections 541 may be omitted. In some implementations, particular ones of components 540 may be omitted or replaced with other components.

Figure 10:
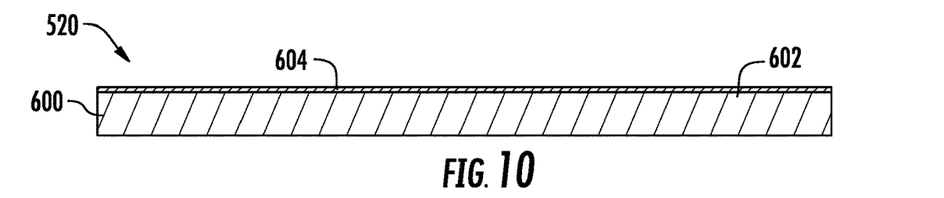
FIGS. 10, 11, 12, 13, 14 and 15 illustrate an example method for forming the example microfluidic package of FIG. 9.
Figure 11:
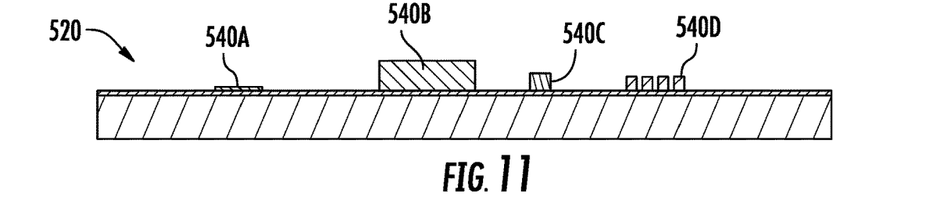
Figure 13:
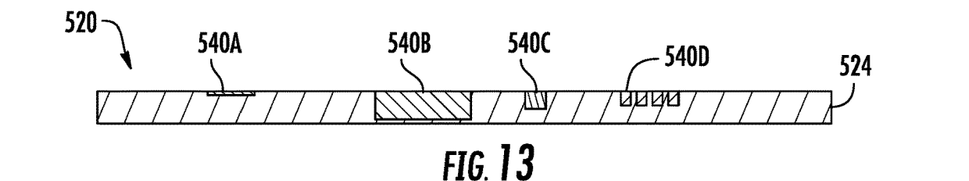
Figure 14:
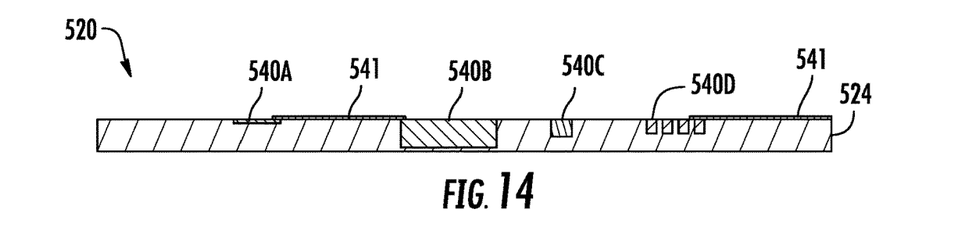
Figure 15:
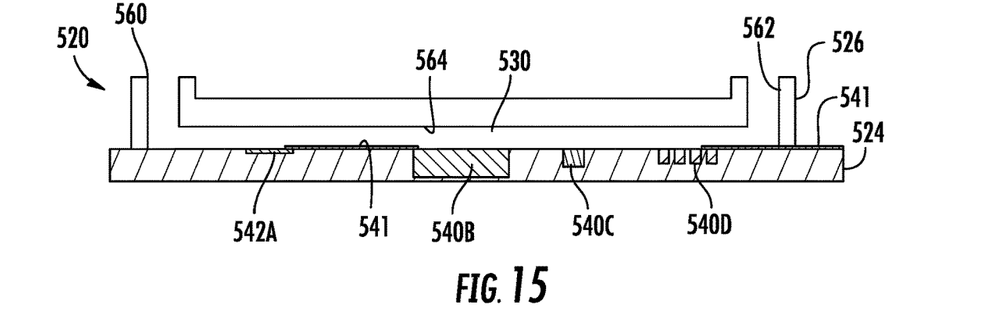

FIGS. 10-15 illustrate an example method for forming microfluidic package 520, shown completed in FIG. 15. As shown by FIG. 10, a carrier 600 is provided. Carrier 600 has a surface 602 covered by a removable or releasable tape 604, such as a thermal release tape. As shown by FIG. 11, components 540 are placed upon the thermal release tape 604.

Figure 12:
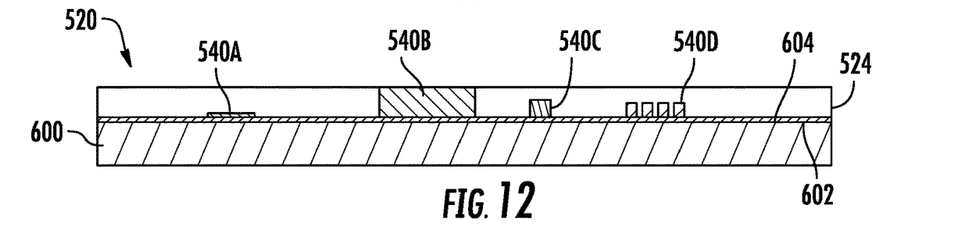

As shown by FIG. 12, an over mold process is carried out, wherein components 540 are covered by a layer of a moldable material that is to form substrate 524. In one implementation, the moldable material comprises an epoxy mold compound. In other implementations, the moldable material comprises other moldable materials. The moldable material is provided with a thickness greater than the greatest thickness of components 540.

As shown by FIG. 13, the moldable material forming substrate 524 is solidified curing or other solidification mechanisms. Following sufficient solidification of the layer forming substrate 524, carrier 600 and release tape 604 are separated from substrate 524. In some implementations, release tape 604 may be omitted where carrier 600 is otherwise removable from the solidified material forming substrate 524. Because component 540 rest upon carrier 600 and release tape 604, the flush positioning of components 540 with respect to the surface of substrate 524 is achieved.

As shown by FIG. 14, electrical connections 541 are formed on top of substrate 524, connecting particular components 540 to one another or to exterior contact pads of the microfluidic package 520. As shown by FIG. 15, the at least one layer of material that forms a fluid passage layer 526 is formed on top of substrate 524. Fluid passage layer 526 forms a fluid passage 530. In one implementation, the material of layer 526 may be formed about a sacrificial material, wherein the sacrificial material is subsequently dissolved or otherwise removed, leaving fluid passage 530. In other implementations, passage 530 may be formed in layer 526 in other manners.

Figure 16:
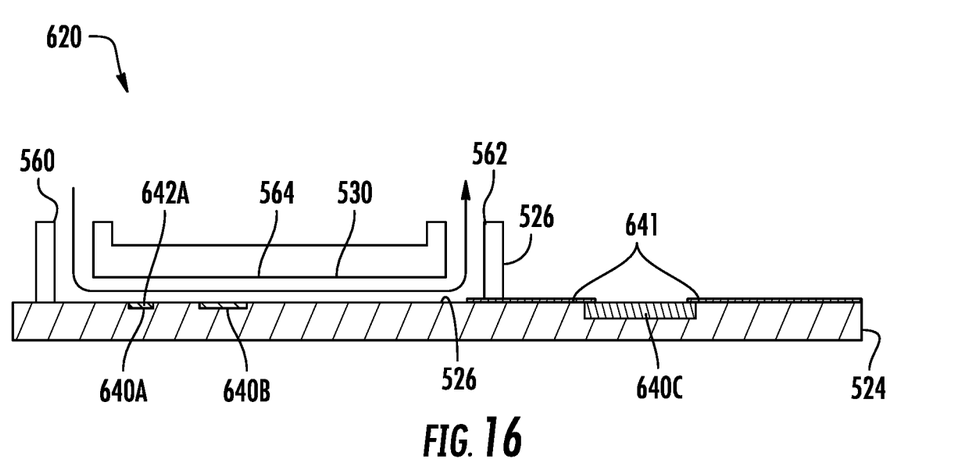
FIG. 16 is a sectional view of an example microfluidic package providing an example integrated sensor system.

FIG. 16 schematically illustrates portions of another example microfluidic package 620. In the example illustrated, microfluidic package 620 comprises an integrated sensor system. Microfluidic package 620 comprises substrate 524, fluid passage layer 526 forming fluid passage 530, components 640A, 640B and 640C (collectively referred to as components 640) and electrical connectors 641. Substrate 524 and fluid passage layer 526 forming fluid passage 530 are similar to corresponding structures of microfluidic passage 520 described above.

As with components 540 of microfluidic package 520, components 640A, 640B and 640C are inset within substrate 524, having corresponding component surfaces 642A, 642B and 642C (collectively referred to as component surfaces 642), respectively. Component surfaces 642 of components 640A and 640B extend adjacent to, directly in contact with, the interior of fluid passage 530. In the example illustrated, such component surfaces 642 extend adjacent to the fluid passage 530 and are flush with surface 526 of substrate 524. Each of such component surfaces 642 are coplanar with one another and coplanar with surface 526. In other implementations, surfaces 642 may not be coplanar with one another and may not flush with surface 526. For example, in some implementations, surfaces 642 may slightly project above or be slightly recessed below surface 526, was still being substantially flush with surface 526.

In the example illustrated, components 640A comprises a semiconductor laser. In one implementation, components 640A has a thickness of at least 30 µm and nominally 50 µm. As shown by FIG. 16, the major surface (the exterior surface having the largest area amongst the exterior surfaces) is exposed to the interior of fluid passage 530.

Components 640B comprises a die in the form of a sensor. In one implementation, component 640B comprises an optical sensor such as a PIN diode or detector. Component 640B has a thickness at least 50 µm and nominally 100 µm.

Component 640C comprises a die in the form of an application-specific integrated circuit. Unlike components 640A and 640B, component 640C is external to the microfluidic passage 530. In operation, component 640A, comprising a semiconductor laser, is used as stimulus. Component 640B, comprising an optical sensor, detects a secondary emission from the fluid sample passing through fluid passage 530. The substantially flush relationship between components 640A and 640B with respect to surface 526 facilitate smooth flow of fluid in fluid passage 530 across each of such components.

Electrical connectors 641 comprises electrically conductive lines, traces or wires that extend from component 640C to each of components 640A and 640B (around component 640B to reach component 640A) and also to external electronics. As discussed above, in some implementations, electrical connectors 641 may alternatively be formed on an underside of substrate 524 or within substrate 524.

In the example illustrated, microfluidic package 620 may be formed in a fashion similar to the process or method shown in FIGS. 10-15. In particular, each of components 640 may be placed upon a carrier 600 or upon release tape 604 supported by a carrier 600. Thereafter, components 640 may be over molded with a layer of material that is to form substrate 524. Once the material forming substrate 524 has solidified, substrate 524 along with the embedded component 640 may be separated from the carrier 600 and release tape 604. Electrical connectors 641 may be mounted to or formed on top of the substrate 524 and substrate 524 in the location shown in FIG. 16. In other implementations, microfluidic package 620 may be formed in other fashions.

Figure 17:
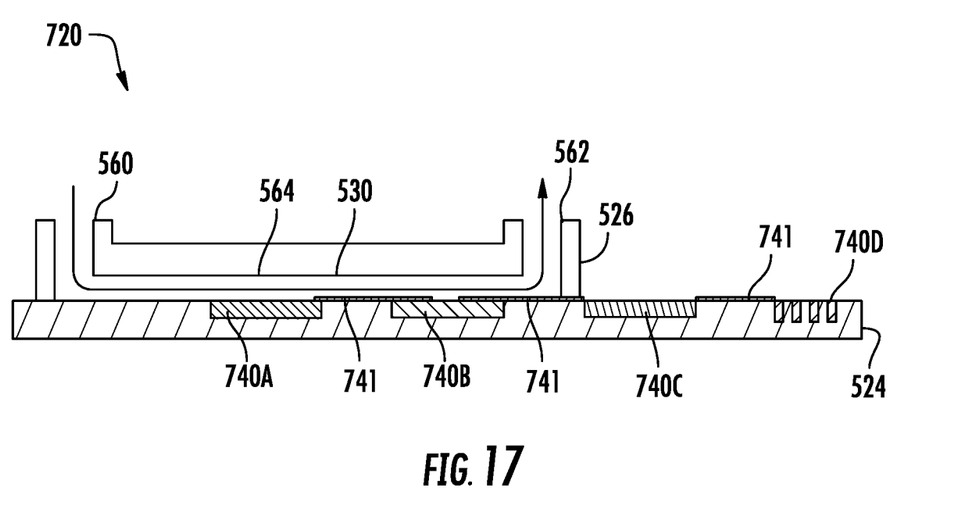
FIG. 17 is a sectional view of an example microfluidic package providing an example chemical an optical sensing device with transceiver.

FIG. 17 is a sectional view schematically illustrating portions of another example microfluidic package of 720. In the example illustrated, microfluidic package 720 comprises a chemical an optical sensing device with transceiver. Microfluidic package 720 comprises substrate 524, fluid passage layer 526 forming fluid passage 530, components 740A, 7406, 740C and 740D (collectively referred to as components 740) and electrical connectors 741. Substrate 524 and fluid passage layer 526 forming fluid passage 530 are similar to corresponding structures of microfluidic passage 520 described above.

As with components 540 of microfluidic package 520, components 740A, 740B, 740C and 640D are inset within substrate 524, having corresponding component surfaces 742A, 742B, 742C and 742D (collectively referred to as component surfaces 742), respectively. Component surfaces 742 of components 740A and 740B extend adjacent to, directly in contact with, the interior of fluid passage 530. In the example illustrated, such component surfaces 742 extend adjacent to the fluid passage 530 and are flush with surface 526 of substrate 524. Each of such component surfaces 742 are coplanar with one another and coplanar with surface 526. In other implementations, surfaces 742 may not be coplanar with one another and may not flush with surface 526. For example, in some implementations, surfaces 742 may slightly project above or be slightly recessed below surface 526, was still being substantially flush with surface 526.

In the example illustrated, component 740A comprises a chemical sensor. For example, in one implementation, component 740A may comprise a chemical sensor such as an ion-sensitive field-effect transistor, or electrical impedance detector. In the example illustrated, component 740A has a thickness of at least 100 μm and nominally 200 μm.

In the example illustrated, component 740B comprises a die the form of an optical sensor. In one implementation, the die comprises a PIN diode or detector. Component 740B has a thickness at least 50 μm and nominally 100 μm.

Components 740C and 740D are located outside of microfluidic passage 530, but are in communication with components 740A and 740B across electrical connectors 741. Component 740C comprises a die in the form of an application-specific integrated circuit. In one implementation, component 740C has a thickness of at least 20 μm and nominally 300 μm. Components 740D comprises an antenna, similar to the antenna provided by component 540D (described above). Component 540D may have a thickness of at least 200 μm and nominally 500 μm.

In operation, fluid flowing through passage 530 is sensed by the chemical sensor provided by component 740A as well as the optical sensor provided by component 740B. The data are signals are transmitted to the application-specific integrated circuit provided by component 740C. The raw data itself or any analysis from such data signals are communicated externally via the antenna provided by component 740D.

In the example illustrated, microfluidic package 720 may be formed in a fashion similar to the process or method shown in FIGS. 10-15. In particular, each of components 740 may be placed upon a carrier 600 or upon release tape 604 supported by a carrier 600. Thereafter, components 740 may be over molded with a layer of material that is to form substrate 524. Once the material forming substrate 524 has solidified, substrate 524 along with the embedded component 640 may be separated from the carrier 600 and release tape 604. Electrical connectors 741 may be formed on top of the substrate 524 in the locations shown in FIG. 17. In other implementations, microfluidic package 720 may be formed in other fashions.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A microfluidic package comprising:
   a fluid passage having an interior including a plurality of interior surfaces;
   a substrate formed of a moldable material and having a substrate surface adjacent an interior surface among the plurality of interior surfaces of the fluid passage; and
   a plurality of heterogeneous components inset in the substrate, the plurality of heterogeneous components having component surfaces adjacent to and that define a portion of the interior surface of the fluid passage and are substantially flush with the substrate surface, and wherein the moldable material is over molded about the plurality of heterogeneous components, wherein the portion of the interior surface of the fluid passage is defined by the substrate surface of the substrate and the component surfaces of the plurality of heterogeneous components as overmolded.

2. The microfluidic package of claim 1, wherein the plurality of heterogeneous components comprise a first component having a first thickness and a second component having a second thickness greater than the first thickness, and wherein the component surfaces of the plurality of heterogeneous components and the substrate surface of the substrate define the portion of the interior surface of the fluid passage such that the component surfaces of the plurality of heterogeneous components and the substrate surface of the substrate are flush with and define part of the interior surface of the fluid passage.

3. The microfluidic package of claim 2, wherein the plurality of heterogeneous components comprise an optical sensor including one of the component surfaces that forms part of an interior surface of the fluid passage, wherein the interior surface of the fluid passage comprises an interior floor surface or interior ceiling surface of the fluid passage.

4. The microfluidic package of claim 1, wherein the plurality of heterogeneous components are each selected from a group of components consisting of:
   a die, a waveguide, an antenna, a semiconductor laser, an application-specific integrated circuit, a chemical sensor, and an optical sensor; and
   wherein the substrate surface of the substrate, as overmolded with the plurality of heterogeneous components, is co-planar with the component surfaces of the plurality of heterogeneous components.

5. The microfluidic package of claim 1, wherein the component surfaces are coplanar, and wherein the plurality of heterogeneous components each include at least one of: a different size, a different shape, and a different function with respect to one another.

6. The microfluidic package of claim 1, wherein the component surfaces are flush with the substrate surface and remaining portions of the interior surface.

7. The microfluidic package of claim 1, wherein the moldable material is an epoxy mold compound which is over molded over and about the plurality of heterogeneous components and that forms the substrate such that the plurality of heterogeneous components are molded into the substrate and the plurality of heterogeneous components are encapsulated by the epoxy mold compound.

8. The microfluidic package of claim 1, wherein the plurality of heterogeneous components are electrically connected with an electrically conductive line on the substrate surface.

9. A microfluidic package comprising:
   a fluid passage having an interior including a plurality of interior surfaces;
   a substrate formed of a moldable material and having a substrate surface adjacent an interior surface among the plurality of interior surfaces of the fluid passage; and
   a plurality of component dies inset in the substrate, the plurality of component dies having component surfaces adjacent to and that define a portion of the interior surface of the fluid passage and are substantially flush with the substrate surface and the plurality of component dies being heterogeneous, and wherein the moldable material is over molded about the plurality of component dies and the portion of the interior surface of the fluid passage is defined by the substrate surface of the substrate and the component surfaces of the plurality of component dies.

10. The microfluidic package of claim 9, wherein the plurality of component dies comprise a first die having a first thickness and a second die having a second thickness greater than the first thickness.

11. The microfluidic package of claim 9, further comprising an external component inset in the substrate exterior to the fluid passage.

12. A method comprising:
   embedding a plurality of heterogeneous components in a substrate surface of a substrate formed of moldable material such that the plurality of heterogeneous components have surfaces substantially flush with the substrate surface, and wherein the moldable material is over molded about the plurality of heterogeneous components; and
   forming a fluid passage having an interior including a plurality of interior surfaces, wherein an interior surface of the plurality of interior surface is adjacent the substrate surface and with the substrate surface and the heterogeneous components defining a portion of the interior surface of the fluid passage.

13. The method of claim 12, wherein the embedding of the heterogeneous components in the substrate surface of the substrate comprises:
   positioning the heterogeneous components on a carrier;
   overmolding the moldable material over and about the heterogeneous components; and
   separating the over molded moldable material and the heterogeneous components from the carrier.

14. The method of claim 12, wherein heterogeneous components are selected from a group of components consisting of:
   a die, a waveguide, an antenna, a semiconductor laser, an application-specific integrated circuit, a chemical sensor, and an optical sensor.

15. The microfluidic package of claim 1, wherein the plurality of heterogeneous components are component dies inset in the substrate.

16. The microfluidic package of claim 9, wherein the moldable material comprises an epoxy mold compound over molded about the plurality of component dies.

17. The microfluidic package of claim 1, wherein each of the plurality of heterogeneous components are between being flush with the substrate surface and 10 micrometers above or below an interior surface of the fluid passage, and the moldable material is over molded about the plurality of heterogeneous components such that the plurality of heterogeneous components are molded into the substrate.

18. The microfluidic package of claim 1, wherein the component surfaces of the plurality of heterogeneous components and the substrate surface of the substrate define the interior surface of the fluid passage, the interior surface being selected from:
   a floor, a ceiling, a sidewall, and a combination thereof.

19. The microfluidic package of claim 1, wherein each of the plurality of heterogeneous components are dissimilar to one another in at least one of size, shape, and function with respect to one another, and the component surfaces of the plurality of heterogeneous components are exposed to the interior of the fluid passage.

20. The microfluidic package of claim 1, wherein the plurality of heterogeneous components include respective heterogeneous components that are flush with the substrate surface, respective heterogeneous components that project above the substrate surface by 10 micrometers or less, and respective heterogeneous components that project below the substrate surface by 10 micrometers or less.

* * * * *